United States Patent
Abe et al.

(10) Patent No.: US 10,545,086 B2
(45) Date of Patent: Jan. 28, 2020

(54) FRICTION COEFFICIENT MEASUREMENT APPARATUS

(71) Applicant: NIPPO SANGYO CO., LTD., Kokubunji-shi (JP)

(72) Inventors: Hironari Abe, Kokubunji (JP); Kosuke Abe, Kokubunji (JP); Noboru Ishikawa, Sapporo (JP)

(73) Assignee: NIPPO SANGYO CO., LTD., Kokubunji-shi (JP)

( * ) Notice: Subject to any disclaimer, the term of this patent is extended or adjusted under 35 U.S.C. 154(b) by 86 days.

(21) Appl. No.: 15/801,758

(22) Filed: Nov. 2, 2017

(65) Prior Publication Data

US 2018/0202917 A1    Jul. 19, 2018

(51) Int. Cl.
*G01N 19/02* (2006.01)

(52) U.S. Cl.
CPC .................................... *G01N 19/02* (2013.01)

(58) Field of Classification Search
CPC ........................................................ G01N 19/02
See application file for complete search history.

(56) References Cited

U.S. PATENT DOCUMENTS

| | | | |
|---|---|---|---|
| 3,392,427 A | 7/1968 | Lane | |
| 6,123,314 A | 9/2000 | Steele | |
| 6,401,576 B1 * | 6/2002 | Wu | B25G 1/066 81/177.4 |
| 2004/0187556 A1 | 9/2004 | Abe | |

(Continued)

FOREIGN PATENT DOCUMENTS

| | | | |
|---|---|---|---|
| FR | 2897909 A1 | 8/2007 | |
| JP | S57-23212 A | 5/1982 | |
| JP | 03189259 A | * 8/1991 | ......... B60G 17/0182 |

OTHER PUBLICATIONS

Extended European Search Report for International Application No. 17203416.7 dated Jun. 7, 2018 (14 pages).

*Primary Examiner* — Paul M. West
(74) *Attorney, Agent, or Firm* — Kratz, Quintos & Hanson, LLP

(57) ABSTRACT

An object of the present invention is to provide a friction coefficient measurement apparatus which measures an angle of relative torsion caused by a friction between a road surface friction measuring rubber attached strip and a road surface and the friction coefficient measurement apparatus which is able to reduce operator taken for work of replacing the road surface friction measuring rubber attached strip with new one.
A friction coefficient measurement apparatus (100) according to the present invention includes a road surface friction measuring rubber attached strip (30) and an attaching bolt (31) which attaches said rubber attached strip (30)(to a main body of the friction coefficient measurement apparatus), a diameter of a large-diameter circular part of an attaching bolt insertion opening (30A) in said rubber attached strip (30) is set (slightly) larger than a diameter of a bolt head of the attaching bolt (31) and a diameter of a small-diameter circular part thereof is set smaller than the diameter of the bolt head of the attaching bolt (31) and is (slightly) larger than the diameter of the bolt shaft thereof, and a spring washer for anti-loosening the attaching bolt (32) and a rubber attached strip fall prevention washer (33) are interposed.

12 Claims, 7 Drawing Sheets

(56) References Cited

U.S. PATENT DOCUMENTS

2005/0016748 A1\* 1/2005 Ritter .................. H05K 5/0208
174/50
2008/0181745 A1 7/2008 Naik
2016/0131592 A1\* 5/2016 Cooper .................. G01N 21/78
356/402

\* cited by examiner

US 10,545,086 B2

FRICTION COEFFICIENT MEASUREMENT APPARATUS

TECHNICAL FIELD

The present invention relates to an apparatus for measuring a friction coefficient of a road surface and, in more detail, relates to a friction coefficient measurement apparatus for measuring an angle of relative torsion caused by a friction between a road surface friction measuring rubber attached strip and a road surface.

BACKGROUND ART

Such a friction coefficient measurement apparatus as mentioned above is proposed by the applicant of the present application (see Patent Literature 1) and is a measurement apparatus which accurately measures a friction coefficient over a wide velocity range from a high velocity to a low velocity and which is easy to carry to a measurement site.

A strip to which road surface friction measuring rubber is attached (hereinafter, referred to as the road surface friction measuring rubber attached strip) of this friction coefficient measurement apparatus is a consumption article and it is requested to exchange the strip with new one every time in a case that the rubber has been worn down due to friction between the rubber and the road surface.

When exchanging the road surface friction measuring rubber attached strip with the new one, first, an attaching bolt which is disposed on one end of the road surface friction measuring rubber attached strip is detached (unscrewed) from a main body of the friction coefficient measurement apparatus. Then, the road surface friction measuring rubber attached strip that a rubber part has been worn down is exchanged with the new one (another road surface friction measuring rubber attached strip that the rubber part is not worn down) and the new one is attached to the main body of the friction coefficient measurement apparatus by screwing the attaching bolt into the friction coefficient measurement apparatus main body.

Here, since the attaching bolt is comparatively small, procedure of detaching the attaching bolt from the friction coefficient measurement apparatus main body and screwing the attaching bolt again into the apparatus main body are complicated. Then, it is necessary to store the attaching bolt which has been detached from measurement apparatus main body somewhere while exchanging the road surface frictional measuring rubber attached strip with the new one and labor taken for performing the work is increased by such the necessity.

Further, it sometimes occurs that the attaching bolt which has been detached from the measurement apparatus main body is fallen downwardly when exchanging the road surface frictional measuring rubber attached strip with the new one. There are many cases where measurement of the friction coefficient using the above-mentioned friction coefficient measurement apparatus is carried out at night, and then, it is difficult to find the attaching bolt in a case that the attaching bolt has been fallen downwardly at night.

Accordingly, although there is a request to reduce the operator taken for performing the procedures of exchanging the road surface friction measuring rubber attached strip with the new one, a technology which is able to apply to such a request has not been proposed yet.

PRIOR ART LITERATURE

Patent Literature

[Patent Literature 1] Japanese Examined Patent Application Publication No. S57-23212

SUMMARY OF INVENTION

Problems to be Solved by Invention

The present invention has been made in view of the above-mentioned issues of related art and aims to reduce the operator taken for performing the work of exchanging the road surface friction measuring rubber attached strip with the new one in the friction coefficient measurement apparatus which measures the angle of relative torsion caused by a friction between a road surface friction measuring rubber attached strip and a road surface.

Constructions of the Invention

In a friction coefficient measurement apparatus (100) according to the present invention, characterized in that the friction coefficient measurement apparatus comprises a road surface friction measuring rubber attached strip (30: a rubber attached strip) and an attaching bolt (31) which attaches the road surface friction measuring rubber attached strip (30) (to a main body of the friction coefficient measurement apparatus 100); that an attaching bolt insertion opening (30A) is formed in the road surface friction measuring rubber attached strip (30), the attaching bolt insertion opening (30A) has a shape formed by overlapping circles of different diameter sizes, a diameter of a large-diameter circular part (30AA) is set so as to be (slightly) larger than a diameter of a bolt head of the attaching bolt (31) and a diameter of a small-diameter circular part (30AB) is set so as to be smaller than the diameter of the bolt head of the attaching bolt (31) and (slightly) larger than a diameter of a bolt shaft thereof; and that a washer for preventing the rubber attached strip from falling (33: hereinafter, referred to as a rubber attached strip fall prevention washer) is interposed between a spring washer (32: an existing spring washer) for anti-loosening the attaching bolt (31), the rubber attached strip fall prevention washer (33) is formed into an annular shape, a notch (33A) is formed therein (in a circumferential direction) and a plurality of projections (33B) which project outward in a radius direction are formed thereon, an opening size (L1) of said notch (33A) is set so as to be (slightly) smaller than an outer diameter of the shaft of the attaching bolt (31) and a maximum distance (L2) between leading ends of the projections (33B) is set so as to be larger than a large diameter of the attaching bolt insertion opening (30A) formed in the road surface friction measuring rubber attached strip (30).

Also, in the friction coefficient measurement apparatus (101) according to the present invention, characterized in that the friction coefficient measurement apparatus comprises a road surface friction measuring rubber attached strip (50: a rubber attached strip) and the attaching bolt (31) which attaches the road surface friction measuring rubber attached strip (50) (to a main body of the friction coefficient measurement apparatus 101); and that an attaching bolt insertion slit (50A) is formed in the road surface friction measuring rubber attached strip (50), the attaching bolt insertion slit (50A) is formed from one side surface toward the center side of the road surface friction measuring rubber attached strip (50) (and is formed in a direction vertical to a longitudinal direction of the road surface friction measuring rubber attached strip 50), the attaching bolt insertion slit (50A) is set so that a width size of which is smaller than a diameter of a bolt head of the attaching bolt (31) and is (slightly) larger than a diameter of a bolt shaft thereof, and (the attaching bolt insertion slit 50A) is set so that a semicircular shape thereof has a diameter size which is smaller than the diameter of the bolt head of the attaching bolt (31) and is (slightly) larger than the diameter of the bolt shaft thereof on the widthways center of the road surface friction measuring rubber attached strip (50).

In the present invention, it is preferable that the road surface friction measuring rubber attached strip (30, 50) is constructed by a magnetic body (for example, iron) and a rubber attached strip holding magnet (34) be provided in the vicinity of the attaching bolt (31).

In addition, in the present invention, it is preferable to include an inclinometer (41) which measures an inclination (of the friction coefficient measurement apparatus 100, 101).

In this case, it is preferable to include an electromagnetic brake (42) (having a function of stopping the operation of the friction coefficient measurement apparatus 100, 101).

Then, in the present invention, it is preferable to include a counter (43) (having a function of measuring and displaying the number of operations or the number of measurements of the friction coefficient measurement apparatus 100, 101).

Further, in the present invention, it is preferable to include a satellite positioning system (44: for example, a global positioning system: GPS).

In addition, in the present invention, it is preferable to include a road surface temperature measurement device (45) which measures a road surface temperature.

Effects of the Invention

According to the present invention having the above-mentioned constructions, in the road surface friction measuring rubber attached strip (30: the rubber attached strip), the attaching bolt (31) is inserted through the large-diameter circular part (30AA) of the attaching bolt insertion opening (30A) formed in the road surface friction measuring rubber attached strip 30) and the road surface friction measuring rubber attached strip (30) is engaged with (locked to) the attaching bolt (31) without unscrewing and detaching the attaching bolt (31) from the main body of the friction coefficient measurement apparatus (100). Then, the road surface friction measuring rubber attached strip (30) is moved relative to the attaching bolt (31) so as to position the shaft of the attaching bolt (31) in the small-diameter circular part (30AB) of the attaching bolt insertion opening (30A) and the attaching bolt (31) is fastened (engaged). Thereby, it is possible to attach the road surface friction measuring rubber attached strip (30) to the main body of the friction coefficient measurement apparatus (100).

On the other hand, when friction measuring rubber (30B) of the road surface friction measuring rubber attached strip (30) has been worn down, the attaching bolt (31) is loosened (unscrewed) in a range that it is not detached from the main body of the friction coefficient measurement apparatus (100), the road surface friction measuring rubber attached strip (30) that the friction measuring rubber (30B) thereof has been worn down is moved so as to position the bolt head of the attaching bolt (31) in the large-diameter circular part (30AA) of the attaching bolt insertion opening (30A). In this state, it is possible to detach the road surface friction measuring rubber attached strip (30) that the friction measuring rubber (30B) thereof has been worn down from the main body of the friction coefficient measurement apparatus (100).

Also, according to the present invention, in the road surface friction measuring rubber attached strip (50: the rubber attached strip), the shaft of the attaching bolt (31) is inserted through an end opening of the attaching bolt insertion slit (50A) formed in the road surface friction measuring rubber attached strip (50), the road surface friction measuring rubber attached strip (50) is moved relative to the attaching bolt (31) (the shaft of the attaching bolt 31 is relatively moved along the attaching bolt insertion slit 50A) so as to position the shaft of the attaching bolt (31) on the widthways center of the road surface friction measuring rubber attached strip (50) (the attaching bolt 31 abuts to the center-side end of the attaching bolt insertion slit 50A and is positioned) and the attaching bolt (31) is fastened, the attaching bolt (31) is screwed, and thereby, it is possible to attach the road surface friction measuring rubber attached strip (50) without detaching the attaching bolt (31) from the main body of the friction coefficient measurement apparatus (101).

On the other hand, when friction measuring rubber (50B) of the road surface friction measuring rubber attached strip (50) has been worn down, the attaching bolt (31) is loosened (unscrewed) in a range that it is not detached from the main body of the friction coefficient measurement apparatus (101), the road surface friction measuring rubber attached strip (50) that the friction measuring rubber (50B) thereof has been worn down is moved and the shaft of the attaching bolt (31) is detached from the attaching bolt insertion slit (50A) in the road surface friction measuring rubber attached strip (50). Thereby, it is possible to detach the road surface friction measuring rubber attached strip (50) that the friction measuring rubber (50B) thereof has been worn down from the main body of the friction coefficient measurement apparatus (101).

As described above, according to the present invention, when exchanging the road surface friction measuring rubber attached strip (30, 50) with the new one, the attaching bolt (31) of the road surface friction measuring rubber attached strip (30, 50) is held in a state of being screwed into the main body of the friction coefficient measurement apparatus (100, 101), and therefore, work of detaching and screwing the attaching bolt (31) are not necessary. Therefore, it is not necessary to separately provide a space for storing the attaching bolt (31) which has been detached from the main body of the friction coefficient measurement apparatus (100, 101) while carrying out the work for exchanging the road surface friction measuring rubber attached strip (30, 50) with the new one.

Further, since the attaching bolt (31) is in a state of being screwed into the main body of the friction coefficient measurement apparatus (100, 101), the attaching bolt (31) does not fall from the main body of the friction coefficient measurement apparatus (100, 101) and the attaching bolt (31) are not lost although the above-mentioned work for exchanging is carried out at night.

In the present invention, the rubber attached strip fall prevention washer (33) in the annular main body part of which the notch (33A) is provided (in the circumferential direction) and on the annular main body part of which the projections (33B) which project in the radius direction outward are formed is interposed between the spring washer (32: the existing spring washer) for anti-loosening the attaching bolt (31) and the bolt head of the attaching bolt (31). Since the opening size (L1) of the notch (33A) formed in the rubber attached strip fall prevention washer (33) is set (slightly) smaller than the outer diameter of the shaft of the attaching bolt (31), when interposing the rubber attached strip fall prevention washer (33) between the spring washer (32) and the bolt head of the attaching bolt (31), the notch (33A) in the rubber attached strip fall prevention washer (33) is manually forced open and the shaft (the bolt shaft) of the attaching bolt (31) is inserted into the forced-open notch (33A).

Since the forced-open notch (33A) is elastically deformed, after the shaft (the bolt shaft) of the attaching bolt (31) has been inserted into the notch (33A), the size of the opening of the notch (33A) returns to a state where it is slightly smaller than the diameter size of the shaft (the bolt shaft) of the attaching bolt (31) and an inner circumferential surface of the rubber attached strip fall prevention washer (33) maintains a state of fastening the attaching bolt (31) with the aid of elastic repulsive force. Therefore, the rubber attached strip fall prevention washer (33) is not separated from the attaching bolt (31).

Then, since the maximum distance (L2) between the leading ends of the projections (33B) of the rubber attached strip fall prevention washer (33) is larger than the large diameter of the attaching bolt insertion opening (30A) in the road surface friction measuring rubber attached strip (30), even when the road surface friction measuring rubber attached strip (30) is in a state of being about to fall downward, the projections (33B) are caught in the attaching bolt insertion opening (30A) in the road surface friction measuring rubber attached strip (30). Therefore, the road surface friction measuring rubber attached strip (30) is prevented from dropping out or falling downward from the attaching bolt (31) or the main body of the friction coefficient measurement apparatus (100, 101).

In the present invention, when the road surface friction measuring rubber attached strip (30, 50) is constructed by the magnetic body (for example, iron) and the rubber attached strip holding magnet (34) is provided in the vicinity of the attaching bolt (31), the road surface friction measuring rubber attached strip (30, 50) is more attracted to the rubber attached strip holding magnet (34) and therefore the road surface friction measuring rubber attached strip (30, 50) is more prevented from being separated from the main body of the friction coefficient measurement apparatus (100, 101).

In addition, in the present invention, when the inclinometer (41) which measures the inclination (of the friction coefficient measurement apparatus (100, 101)) and the electromagnetic brake (42) (having the function of stopping the operation of the friction coefficient measurement apparatus (100, 101)) are included, in a case where the inclination of at least a predetermined angle has been measured by the inclinometer (41) in a state where the friction coefficient measurement apparatus (100, 101) is in operation, the electromagnetic brake (42) operates and stops the operation of the friction coefficient measurement apparatus (100, 101).

In addition, also in a case where the friction coefficient measurement apparatus (100, 101) which is in operation has been manually lifted, the inclination of at least the predetermined angle is measured by the inclinometer (41), the electromagnetic brake (42) operates and stops the operation of the friction coefficient measurement apparatus (100, 101).

Thereby, safety and accuracy in measurement of the friction coefficient measurement apparatus (110, 101) are secured and the safety of the operator is secured.

Then, in the present invention, when a counter (43) (having the function of measuring and displaying the number of operations or the number of measurements of the friction coefficient measurement apparatus (100, 101)) is included, it is possible to obtain an index for indicating to what extent the friction measuring rubber (30B, 50B) of the road surface friction measuring rubber attached strip (30, 50) in the friction coefficient measurement apparatus (100, 101) is worn down by the number of times displayed by the counter (43) and therefore it is possible to grasp the timing of replacing the road surface friction measuring rubber attached strip (30, 50) with the new one.

Further, in the present invention, when the satellite positioning system (44: for example, the global positioning system: GPS) is included, it is possible to accurately determine a position where the friction coefficient has been measured.

In addition, in the present invention, when the road surface temperature measurement device (45) which measures the temperature of the road surface is included, it is possible to measure the temperature of the road surface when measuring the friction coefficient of the road surface and thereby to determine the accurate friction coefficient that an important parameter which is called the road surface temperature has been taken into consideration.

MODES FOR CARRYING OUT THE INVENTION

In the following, preferred embodiments of the present invention will be described with reference to the appended drawings.

First, the friction coefficient measurement apparatuses 100 and 101 to which the present invention is applied will be described with reference to FIG. 1 and FIG. 2.

Figure 1:
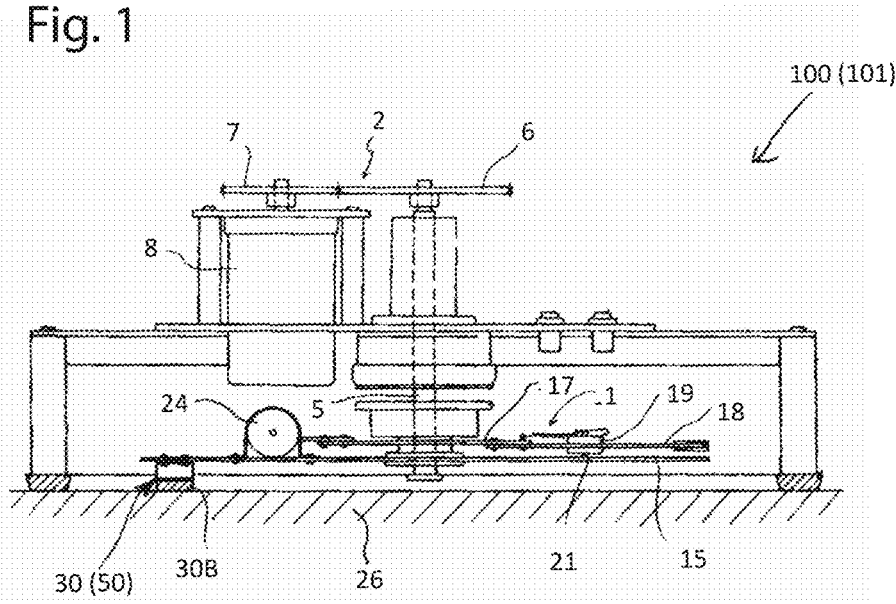
FIG. 1 is a diagram illustrating one example of an overview of a friction coefficient measurement apparatus according to one embodiment of the present invention.

In FIG. 1, the friction coefficient measurement apparatuses 100 (101) according to each embodiment includes a friction measurement unit 1, a drive unit 2 which is a rotational driving source and so forth. The friction measurement unit 1 rotates a shaft 5, a disk-shaped main body 15 and a disk 17 which is a rotor by a motor 8 via gears 6 and 7. As illustrated in FIG. 2, the main body 15 and the disk 17 are coupled together in a tangential direction of the main body 15 by a spring 16.

As illustrated in FIG. 1, a guide plate 18 and a pen holder 19 which is slidable in a radius direction are disposed on the disk 17. As illustrated in FIG. 2, the pen holder 19 is coupled to the disk 17 by a spring 20. A pen 21 (FIG. 1) used for recording measured values on a recording paper 27 is disposed on the center of the pen holder 19.

Figure 2:
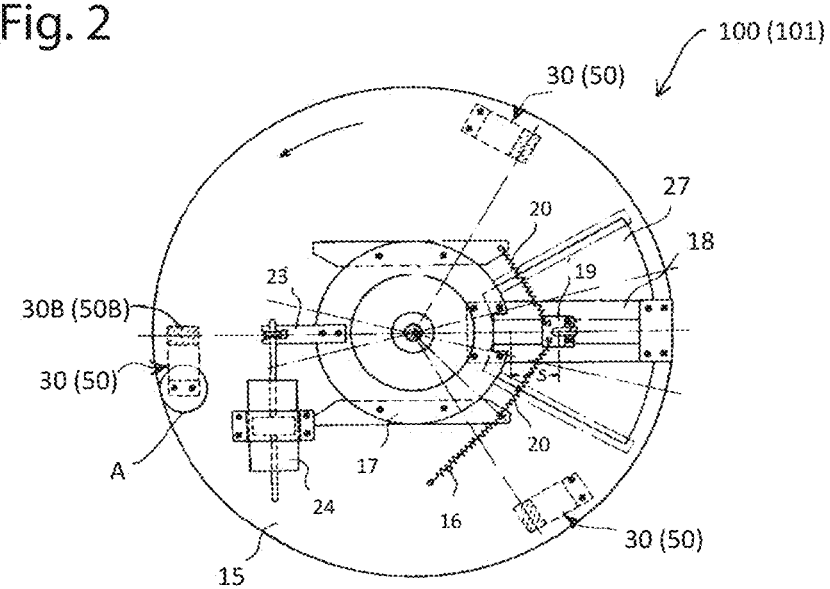
FIG. 2 is a plan view of the friction coefficient measurement apparatus illustrated in FIG. 1.

In FIG. 2, an arm 23 is attached to the disk 17 on the side (on the left side in FIG. 2) opposite to the guide plate 18 and the arm 23 is coupled to a damper 24. The damper 24 is fixed to the main body 15 and functions as a damping device which damps a torsional vibration generated by the disk 17 and the spring 20.

The road surface friction measuring rubber attached strips 30 (50) (so called "sliders") are attached to a lower surface of the main body 15 on the same circumference, for example, at three positions.

In FIG. 1, when the friction measuring rubber 30B (50B) (of each of the road surface friction measuring rubber attached strips 30 (50)) comes into contact with a road surface 26, acceleration which works in a stop direction acts to rotation of the disk-shaped main body 15 to which the friction measuring rubber 30B (50B) is integrally attached caused by friction between the friction measuring rubber 30B (50B) and the road surface 26.

The acceleration which works in the stop direction also acts to the disk 17 which rotates by being coupled with the main body 15 via the spring 16 in association with the above-mentioned operation. On this occasion, torsion corresponding to the magnitude of the frictional force between the road surface 26 and the friction measuring rubber 30B (50B) is generated between the main body 15 and the disk 17. Then, the main body 15 and the disk 17 rotate in synchronization with each other at mutual relative positions where elastic force of the spring 16 and the friction force acting to the friction measuring rubber 30B (50B) are well-balanced.

A friction coefficient $\mu$ of the road surface 26 which is determined in accordance with a tangential velocity V measured by the friction coefficient measurement apparatus 100 (101) is proportional to a relative torsion angle $\theta$ between the main body 15 and the disk 17 and it is possible to obtain the friction coefficient $\mu$ by measuring the relative torsion angle $\theta$. In addition, it is possible to express a tangential velocity V (the measured velocity V) of the friction measurement rubber 30B (50B) as a function of a displacement amount S (FIG. 2) in the radius direction of the spring 20.

When the relative torsion angle $\theta$ between the main body 15 and the disk 17 and the displacement amount S in the radius direction of the spring 20 are recorded by handwriting on the recording paper 27, it becomes possible to calculate the friction coefficient $\mu$ and the measured velocity V from the recorded torsion angle $\theta$ and displacement amount S by the friction coefficient measurement apparatus 100 (101).

In the illustrated embodiment, a relation between the tangential velocity V of the friction measuring rubber 30B (50B) of the road surface friction measuring rubber attached strip 30 (50) and the displacement amount S of the spring 20 and a relation between the friction coefficient $\mu$ and the relative torsion angle $\theta$ are calibrated in advance and thereby it is possible to automatically record the friction coefficient $\mu$ of the road surface 26 and the relative velocity V on the recording paper 27 and it is possible to obtain a change in friction coefficient $\mu$ ranging from a high velocity to a low velocity by one-time measurement.

As mentioned above, the friction measuring rubber 30B (50B) of the road surface friction measuring rubber attached strip 30 (50) is the consumption article. Accordingly, when measurement of the road surface friction is repetitively performed and the rubber is worn down due to the friction between the rubber 30B (50B) and the road surface 26, it is requested to replace the road surface friction measuring rubber attached strip 30 (50) that the friction measuring rubber 30B (50B) thereof has been worn down with the new one.

The part A in FIG. 2 is a place where the road surface friction measuring rubber attached strip 30 (50) is attached to the disk-shaped main body 15 of the friction coefficient measurement apparatus 100 (101) and the attaching bolt 31 is provided on the attachment place A.

Figure 3A:
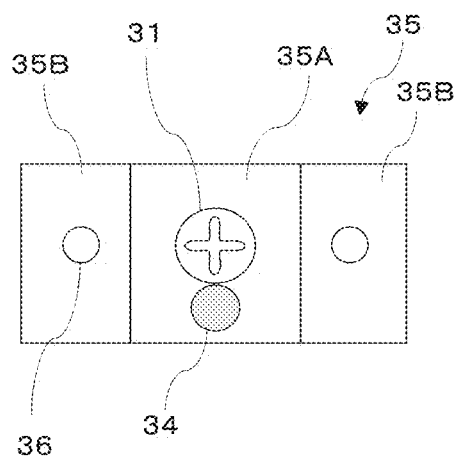
FIG. 3A is an enlarged explanatory diagram illustrating one example of a part A in FIG. 2.
Figure 3B:
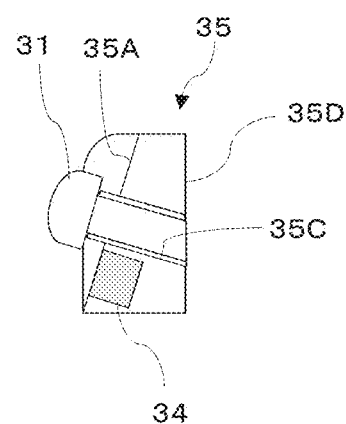
FIG. 3B is an enlarged explanatory diagram illustrating one example of the part A in FIG. 2.

In FIG. 3A and FIG. 3B, the attaching bolt 31 is screwed into a holder 35 which is fixed to the main body 15 (see FIG. 1 and FIG. 2: not illustrated in FIG. 3A and FIG. 3B) and thereby attaches the road surface friction measuring rubber attached strip 30 (50) (not illustrated in FIG. 3A and FIG. 3B) (to the main body 15). In FIG. 3A and FIG. 3B, a symbol 36 denotes a bolt which fixes the holder 35 to the main body 15 side.

A rubber attached trip attachment part 35A is formed on the center (the center in a crosswise direction in FIG. 3A) of the holder 35. Parts 35B on the both sides of the rubber attached strip attachment part 35A (the right and left sides of the rubber attached strip attachment part 35A in FIG. 3A) are formed as members of a uniform thickness. On the other hand, the thickness of the rubber attached strip attachment part 35A is not uniform as illustrated in FIG. 3B and the thickness is gradually reduced linearly from one end (a lower end in FIG. 3B) toward the other end (an upper end in FIG. 3B).

A screw hole 35C (FIG. 3B) is formed in the center (the center in the crosswise direction in FIG. 3A) of the rubber attached strip attachment part 35A of the holder 35 so as to screw the attaching bolt 31 into the screw hole 35C. The rubber attached strip attachment part 35A is inclined relative to a bottom surface 35D (an attachment surface to the main body 15 side: extending in a vertical direction in FIG. 3B) of the holder 35 as illustrated in FIG. 3B.

In FIG. 3A, the rubber attached strip holding magnet 34 is provided in the vicinity of the attaching bolt 31 (the attachment place A in FIG. 2: under the attaching bolt 31 in FIG. 3A and FIG. 3B) and attracts the road surface friction measuring rubber attached strip 30 (50) which is constructed by the magnetic body (for example, iron) other than the rubber part. Even in a case where the attaching bolt 31 has been detached (unscrewed) from the screw hole 35C, the road surface friction measuring rubber attached strip 30 (50) is attracted to the rubber attached strip holding magnet 34 and therefore separation (falling) of the road surface friction measuring rubber attached strip 30 (50) from the main body 15 is prevented.

The rubber attached strip holding magnet 34 is embedded in the rubber attached strip attachment part 35A of the holder 35 and the shape thereof may be cylindrical as illustrated in FIG. 3A and FIG. 3B or may be rectangular parallelepiped (not illustrated).

A situation where the road surface friction measuring rubber attached strip 30 is attached to the friction coefficient measurement apparatus 100 by the attaching bolt 31 in a first embodiment of the present invention will be described with reference to FIG. 4A, FIG. 4B, FIG. 5A, FIG. 5B, FIG. 6A, FIG. 6B, FIG. 7 and FIG. 8.

Figure 4A:
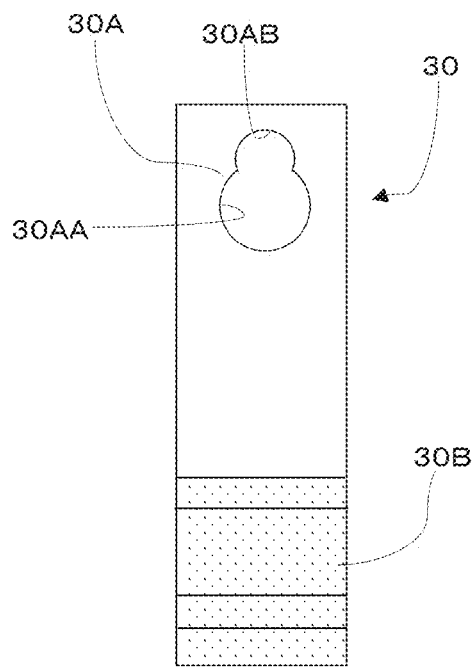
FIG. 4A is a diagram illustrating one example of a road surface friction measuring rubber attached strip used in a first embodiment of the present invention.
Figure 4B:
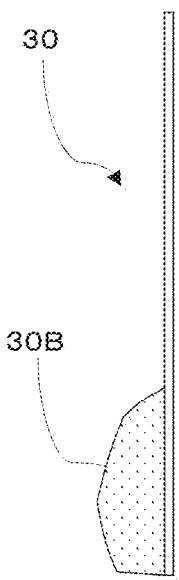
FIG. 4B is a diagram illustrating one example of the road surface friction measuring rubber attached strip used in the first embodiment of the present invention.

As illustrated in FIG. 4A and FIG. 4B, the friction measuring rubber 30B is attached to one end (a lower end in FIG. 4A and FIG. 4B) of the road surface friction measuring rubber attached strip 30 by a well-known manner (for example, adhesion, welding and so forth) and the vicinity of the other end (an upper end in FIG. 4A and FIG. 4B) of the road surface friction measuring rubber attached strip 30 is constructed as an attachment part to the main body 15 side.

When the friction measuring rubber 30B is worn down, the road surface friction measuring rubber attached strip 30 that the friction measuring rubber 30B thereof has been worn down is exchanged with the new one (another road surface friction measuring rubber attached strip 30 that the friction measuring rubber 30B thereof is not worn down).

As illustrated in FIG. 4B, the friction measuring rubber 30B is gradually increased in thickness toward a leading end (the rubber 30B side end: the lower end in FIG. 4B) of the road surface friction measuring rubber attached strip 30 and has a sufficient thickness in the vicinity of the leading end thereof.

As illustrated in FIG. 4A, the insertion opening 30A into which the attaching bolt 31 is to be inserted is formed in the attachment part in the vicinity of the other end of the road surface friction measuring rubber attached strip 30 (the end which is opposite to the end to which the rubber 30B is attached: the upper end in FIG. 4A).

The attaching bolt insertion opening 30A is formed into a shape obtained by overlapping the circles of different diameter sizes, the small-diameter circular part 30AB is disposed on the upper part (in FIG. 4A) and the large-diameter circular part 30AA is disposed on the lower part (in FIG. 4A).

The diameter of the large-diameter circular part 30AA is set slightly larger than the diameter of the bolt head of the attaching bolt 31 and the diameter of the small-diameter circular part 30AB is set smaller than the diameter of the bolt head of the attaching bolt 31 and slightly larger than the diameter of the bolt shaft thereof.

Figure 5A:
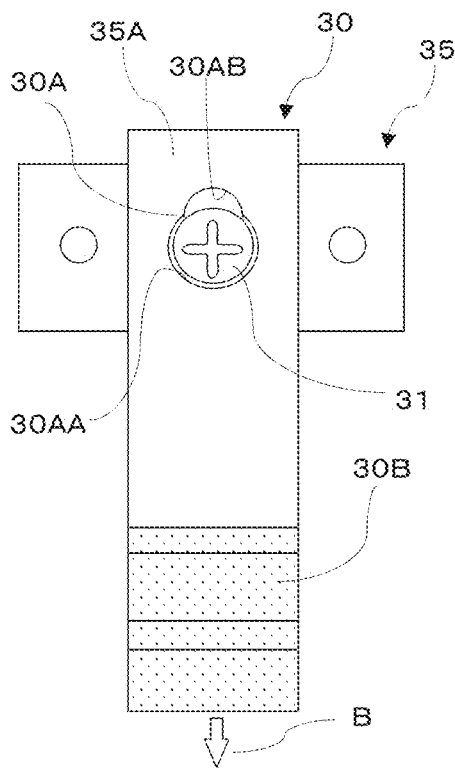
FIG. 5A is an explanatory diagram illustrating one example of a state where the road surface friction measuring rubber attached strip illustrated in FIG. 4A and FIG. 4B has been locked to an attaching bolt.
Figure 5B:
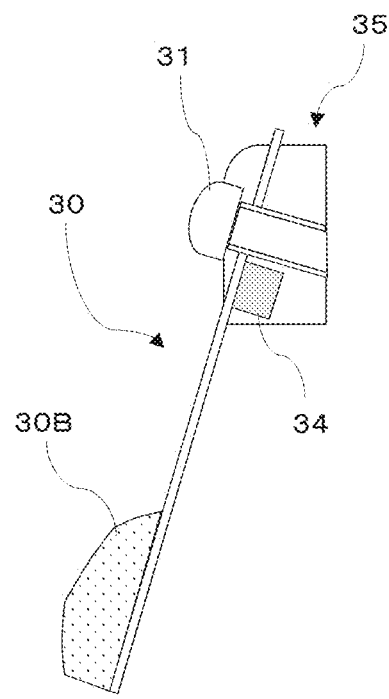
FIG. 5B is an explanatory diagram illustrating one example of the state where the road surface friction measuring rubber attached strip illustrated in FIG. 4A and FIG. 4B has been locked to the attaching bolt.

When attaching the road surface friction measuring rubber attached strip 30 to the main body 15, the bolt head of the attaching bolt 31 is inserted into the large-diameter circular part 30AA of the attaching bolt insertion opening 30A in the road surface friction measuring rubber attached strip 30 and the road surface friction measuring rubber attached strip 30 is caught on (locked to) the attaching bolt 31. At this time, the vicinity of the end on the attachment part side (the side opposite to the rubber 30B) of the road surface friction measuring rubber attached strip 30 faces the rubber attached strip attachment part 35A of the holder 35. In FIG. 5A, the rubber attached strip attachment part 35A is located behind the road surface friction measuring rubber attached strip 30. Since the rubber attached strip attachment part 35A is not illustrated in FIG. 5A, a leader line of the symbol "35A" is indicated by a dotted line).

Figure 6A:
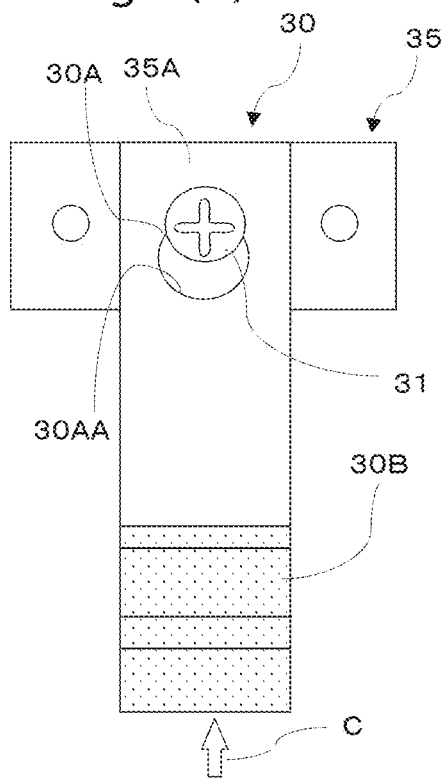
FIG. 6A is an explanatory diagram illustrating one example of a state where the road surface friction measuring rubber attached strip is moved from the state in FIG. 5A and FIG. 5B and the attaching bolt has been screwed into the main body of the friction coefficient measurement apparatus.
Figure 6B:
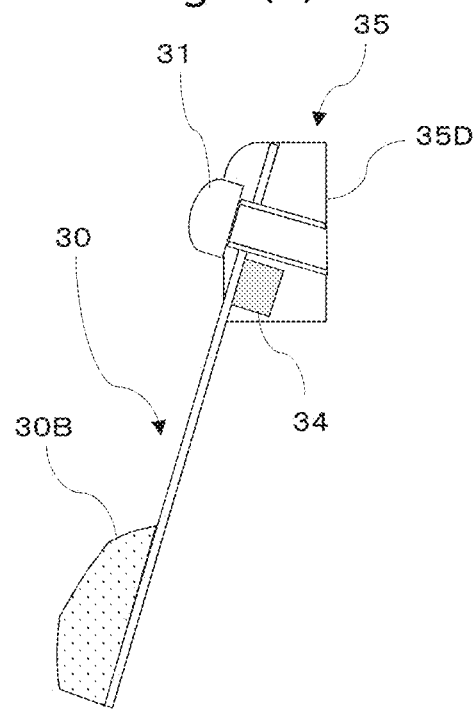
FIG. 6B is an explanatory diagram illustrating one example of the state where the road surface friction measuring rubber attached strip is moved from the state in FIG. 5A and FIG. 5B and the attaching bolt has been screwed into the main body of the friction coefficient measurement apparatus.

The road surface friction measuring rubbed attached strip 30 is moved (pulled) from the state illustrated in FIG. 5A in an arrow B direction (downward in FIG. 5A) in FIG. 5A and the shaft of the attaching bolt 31 is positioned in the small-diameter circular part 30AB (the upper part of the opening 30A) of the attaching bolt insertion opening 30A (a state in FIG. 6A and FIG. 6B). The attaching bolt 31 is fastened in the state in FIG. 6A and FIG. 6B and thereby the road friction measuring rubber attached strip 30 is attached to the main body 15 of the friction coefficient measurement apparatus 100 via the holder 35.

The attaching bolt 31 and the rubber attached strip attachment part 35A of the holder 35 are disposed so as to be inclined relative to the bottom surface 35D which is the attachment surface of the holder 35 to the main body 15 side as mentioned above with reference to FIG. 3B. Accordingly, in FIG. 6B which illustrates a state where the road surface friction measuring rubber attached strip 30 is attached to the holder 35, the friction measuring rubber 30B which is provided on a leading end of the road surface friction measuring rubber attached strip 30 is disposed closer to the not illustrated road surface relative to the attachment surface (the bottom surface 35D of the holder 35) on the main body 15 side. Here, the left side in FIG. 6B is the road surface side.

When detaching the road surface friction measuring rubber attached strip 30 that the friction measurement rubber 30B thereof has been worn down, the attaching bolt 31 is loosened (unscrewed) in a range that the attaching bolt 31 is not detached from the holder 35 in FIG. 6A. Then, the road surface friction measuring rubber attached strip 30 is moved in an arrow C direction in FIG. 6A (upward in FIG. 6A) so as to position the bolt head of the attaching bolt 31 in the large-diameter circular part 30AA of the attaching bolt insertion opening 30A as illustrated in FIG. 5A. Then, the road surface friction measuring rubber attached strip 30 is moved (pulled up) in a direction vertical to the drawing of FIG. 5A and in a spectator-side direction such that the attaching bolt 31 passes through the large-diameter circular part 30AA of the attaching bolt insertion opening 30A and thereby the road surface friction measuring rubber attached strip 30 is detached from the main body of the friction coefficient measurement apparatus 100.

According to the illustrated first embodiment, since the road surface friction measuring rubber attached strip 30 is attached to and detached from the main body of the friction coefficient measurement apparatus 100 in the above-mentioned manner, when performing the work of replacing the road surface friction measuring rubber attached strip 30 with the new one, the attaching bolt 31 is held in a state of being not detached from the holder 35 (in a state of being screwed into the holder 35) and therefore it is not requested to perform the work of unscrewing the attaching bolt 31, detaching the attaching bolt 31 and then again screwing the attaching bolt 31 into the holder 35 (after the road surface friction measuring rubber attached strip 30 has been attached or detached). Therefore, it is not requested to separately provide the space for storing the attaching bolt 31 which has been detached from the main body 15 side while performing the work of replacing the road surface friction measuring rubber attached strip 30 with the new one and also management man-day for provision of the space is not taken.

Further, since the attaching bolt 31 is in a state of being screwed to the main body 15 side, the attaching bolt 31 does not fall from the main body 15 side and there is no fear of losing the attaching bolt 31 even in the night work.

In addition, since the road surface friction measuring rubber attached strip 30 is attracted to the rubber attached strip holding magnet 34, separation of the road surface friction measuring rubber attached strip 30 from the main body 15 side is prevented.

In addition, since the road surface friction measuring rubber attached strip 30 is attached to the main body 15 of the friction coefficient measurement apparatus 100 via the holder 35, it is possible to select a distance between the friction measuring rubber 30B and the road surface 26 and a contact angle of the friction measuring rubber 30B relative to the road surface 26 by appropriately setting the inclination of the bottom surface 35D (the attachment surface) of the rubber attached strip attachment part 35A of the holder 35.

Here, when the road surface friction measuring rubber attached strip 30 is moved relative to the attaching bolt 31 for some reason and the attaching bolt 31 is positioned in the large-diameter circular part 30AA of the attaching bolt insertion opening 30A, it is feared that the road surface friction measuring rubber attached strip 30 may fall from the main body 15.

Figure 8:
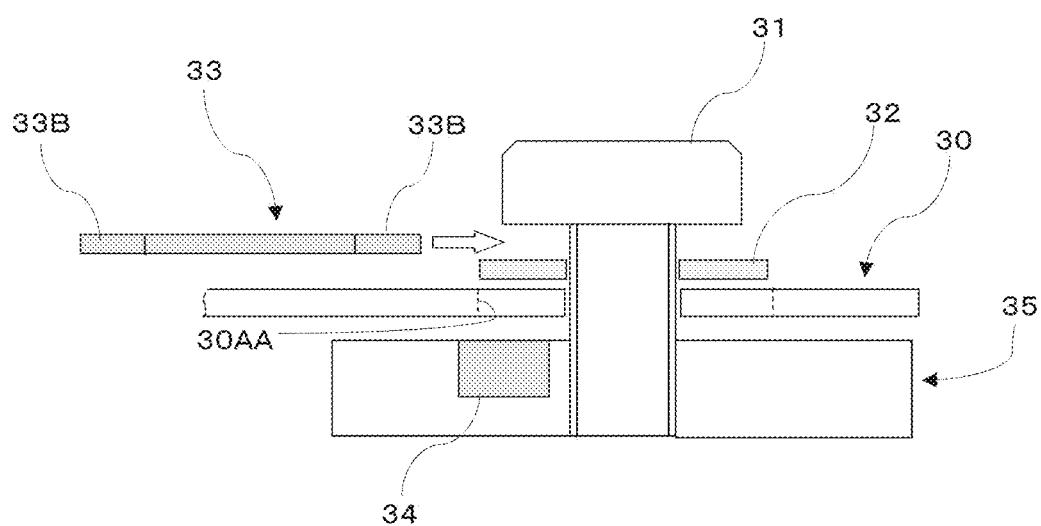
FIG. 8 is an explanatory diagram illustrating one example of a position where the rubber attached strip fall prevention washer illustrated in FIG. 7 is attached.

Although not clearly illustrated in FIG. 5A, FIG. 5B, FIG. 6A and FIG. 6B, in the illustrated first embodiment, the spring washer 32 (the existing spring washer) for anti-loosening the attaching bolt 31 is provided (see FIG. 8).

Figure 7:
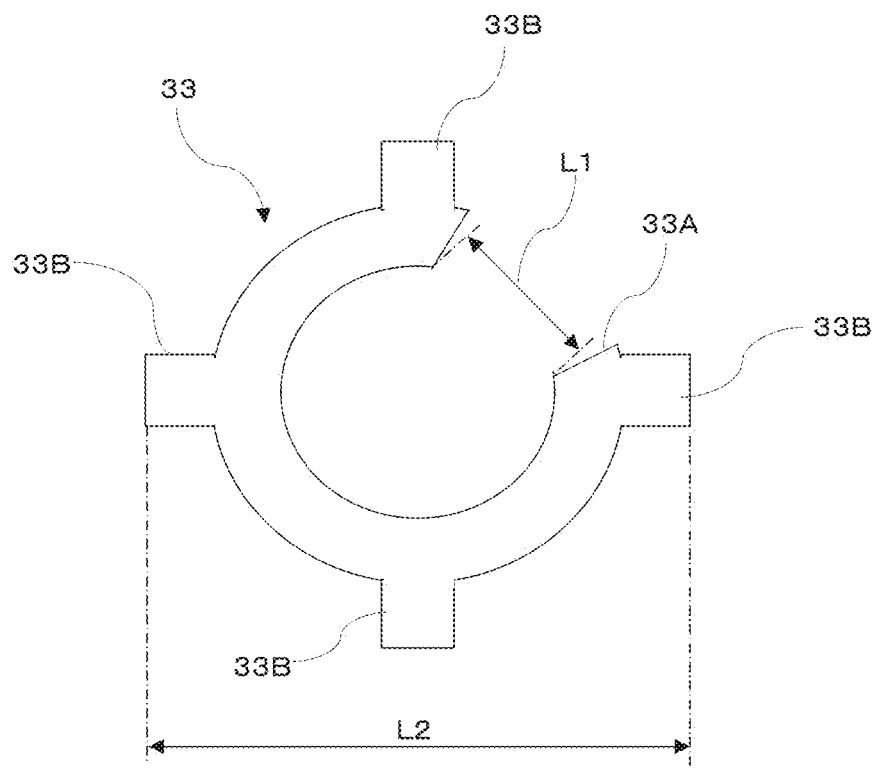
FIG. 7 is a plan view illustrating one example of a rubber attached strip fall prevention washer used in the first embodiment.

In addition, in the illustrated first embodiment, in order to prevent the road surface friction measuring rubber attached strip 30 from dropping out of the main body 15 side of the friction coefficient measurement apparatus 100, the rubber attached strip fall prevention washer 33 is provided as illustrated in FIG. 7 and FIG. 8.

In FIG. 7, the rubber attached strip fall prevention washer 33 has the main body part which is annular as a whole and the notch 33A is formed in one part of the main body part in its circumferential direction. Then, the plurality (four) of projections 33B which project outward in the radius direction are formed on the main body part at equally separated positions in its circumferential direction.

The opening size L1 of the notch 33A is set (slightly) smaller than the outer diameter of the shaft of the attaching bolt 31 and the distance L2 between the leading ends of the two projections 33B which are disposed at mutually facing positions is set larger than the diameter of the large-diameter circular part 30AA (see FIG. 4A) of the attaching bolt insertion opening 30A in the road surface friction measuring rubber attached strip 30.

The diameter of the inner circumferential surface of the rubber attached strip fall prevention washer 33 is set the same as the diameter of the inner circumferential surface of the existing spring washer 32.

As illustrated in FIG. 8, the rubber attached strip fall prevention washer 33 is interposed between the existing spring washer 32 and the bolt head of the attaching bolt 31. Then, the rubber attached strip fall prevention washer 33 is set to a size which makes it possible to nip and hold the rubber attached strip fall prevention washer 33 by the existing spring washer 32 and the bolt head of the attaching bolt 31.

In FIG. 8, the rubber attached strip fall prevention washer 33 and the existing spring washer 32 are interposed between the bolt head of the attaching bolt 31 and the road surface friction measuring rubber attached strip 30 and the rubber attached strip fall prevention washer 33 is interposed between the existing spring washer 32 and the bolt head of the attaching bolt 31.

When disposing the rubber attached strip fall prevention washer 33 between the existing spring washer 32 and bolt head of the attaching bolt 31, the notch 33A (FIG. 7) is pressed in a diameter expanding direction and is elastically deformed to such an extent that the opening size L1 of the notch 33A becomes larger than the diameter size of the shaft (the bolt shaft) of the attaching bolt 31 and the shaft of the attaching bolt 31 is inserted through the notch 33A.

After the shaft (the bolt shaft) of the attaching bolt 31 has been inserted through the notch 33A, pressing of the notch 33A (FIG. 7) in the diameter expanding direction is stopped. Thereby, the opening of the notch 33A is returned to a state of being slightly smaller than the diameter size of the shaft (the bolt shaft) of the attaching bolt 31 with the aid of the elastic repulsive force of the rubber attached strip fall prevention washer 33. As a result, since the inner circumferential surface of the rubber attached strip fall prevention washer 33 maintains a state of fastening the attaching bolt 31 with the aid of the elastic compulsive force, the road surface friction measuring rubber attached strip 30 is not separated from the attaching bolt 31.

As mentioned above, the maximum distance L2 between the leading ends of the two facing projections 33B of the rubber attached strip fall prevention washer 33 is set larger than the diameter of the large-diameter circular part 30AA of the attaching bolt insertion opening 30A in the road surface friction measuring rubber attached strip 30. Therefore, even in a case where the road surface friction measuring rubber attached strip 30 is in a state of being about to fall (upward in FIG. 8), the projections 33B are caught in the attaching bolt insertion opening 30A in the road surface friction measuring rubber attached strip 30.

Therefore, the road surface friction measuring rubber attached strip 30 does not drop out of the attaching bolt 31 or does not fall downward.

Next, a second embodiment of the present invention will be described with reference to FIG. 9A, FIG. 9B, FIG. 10A, FIG. 10B, FIG. 11A and FIG. 11B. More specifically, in the second embodiment, a manner of attaching the road surface friction measuring rubber attached strip 50 to the friction coefficient measurement apparatus 101 by the attaching bolt 31 will be described.

The friction coefficient measurement apparatus 101 according to the second embodiment is different from the friction coefficient measurement apparatus 100 according to the first embodiment in the constructions of the road surface friction measuring rubber attached strip 50. In addition, the friction coefficient measurement apparatus 101 according to the second embodiment does not include the rubber attached strip fall prevention washer 33 in the first embodiment.

Figure 9A:
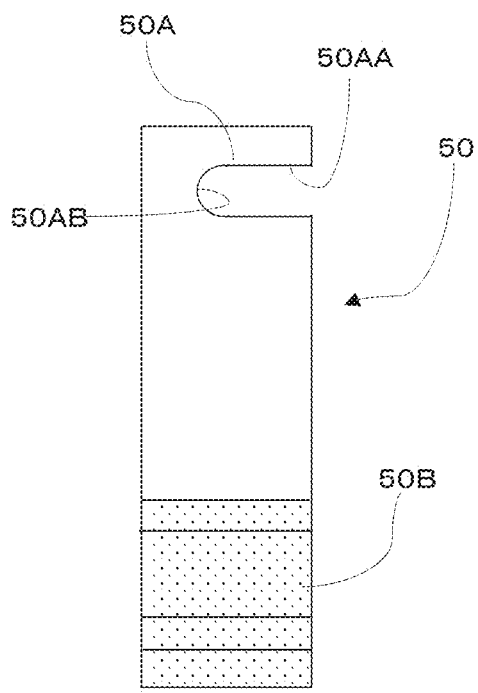
FIG. 9A is an explanatory diagram illustrating one example of a road surface friction measuring rubber attached strip used in a second embodiment of the present invention.
Figure 9B:
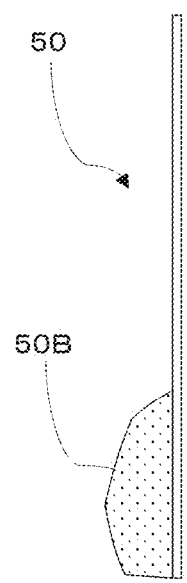
FIG. 9B is an explanatory diagram illustrating one example of the road surface friction measuring rubber attached strip used in the second embodiment of the present invention.

As illustrated in FIG. 9A and FIG. 9B, the friction measuring rubber 50B is attached to one end (the lower end in FIG. 9A and FIG. 9B) of the road surface friction measuring rubber attached strip 50 used in the second embodiment by the well-known manner (for example, adhesion, welding and so forth). The vicinity of the other end (the upper end in FIG. 9A and FIG. 9B) of the road surface friction measuring rubber attached strip 50 is constructed as an attachment part to the main body 15 side. The friction measuring rubber 50B according to the second embodiment has constructions and characteristics which are the same as those of the friction measuring rubber 30B of the road surface friction measuring rubber attached strip 30 according to the first embodiment.

Similarly to the case of the first embodiment, when the friction measuring rubber 50B has been worn down, the road surface friction measuring rubber attached strip 50 that the friction measuring rubber 50B thereof has been worn down is replaced with the new one (another road friction measuring rubber attached strip 50 that the friction measuring rubber 50B thereof is not worn down.

As illustrated in FIG. 9A, the attaching bolt insertion slit 50A into which the attaching bolt 31 is to be inserted is formed in the attachment part in the vicinity of the other end (the end which is opposite to the end that the friction measuring rubber 50B is attached: the upper end in FIG. 9A) of the road surface friction measuring rubber attached strip 50.

The attaching bolt insertion slit 50A is formed from one side surface (a right side surface in FIG. 9A) of the road surface friction measuring rubber attached strip 50 toward the leftward center side and is formed in a direction vertical to a longitudinal direction of the road surface friction measuring rubber attached strip 50.

The attaching bolt insertion slit 50A includes an insertion part 50AA which is formed from one side surface (the right side surface in FIG. 9A) of the road surface friction measuring rubber attached strip 50 toward the center side (leftward in FIG. 9A) up to the widthways center (of the road surface friction measuring rubber attached strip 50) having a predetermined width size and a semicircular central part 50AB which is formed contiguously to the insertion part 50AA and has a predetermined diameter size on the widthways center (of the road surface friction measuring rubber attached strip 50).

Here, both of the width size of the insertion part 50AA and the diameter size of the central part 50AB of the attaching bolt insertion slit 50A are set sizes which are smaller than the diameter of the bolt head of the attaching bolt 31 and slightly larger than the diameter of the bolt shaft thereof.

The road surface friction measuring rubber attached strip 50 is attached to the main body 15 (see FIG. 1 and FIG. 2) of the friction coefficient measurement apparatus 101 via the holder 35 which is the same as that which has been mentioned above with reference to FIG. 3A and FIG. 3B and so forth similarly to the first embodiment.

Figure 10A:
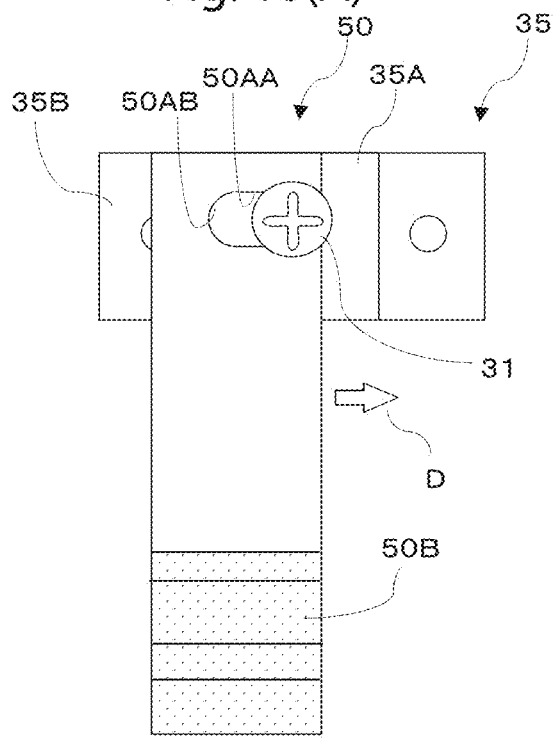
FIG. 10A is an explanatory diagram illustrating one example of a state where the road surface friction measuring rubber attached strip illustrated in FIG. 9A and FIG. 9B has been locked to the attaching bolt.
Figure 10B:
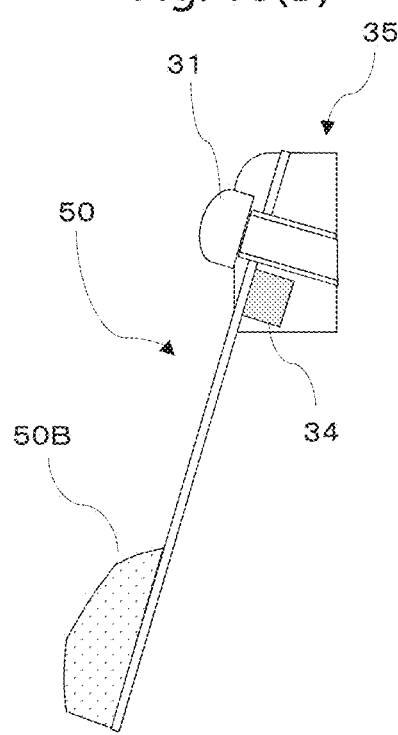
FIG. 10B is an explanatory diagram illustrating one example of the state where the road surface friction measuring rubber attached strip illustrated in FIG. 9A and FIG. 9B has been locked to the attaching bolt.

When attaching the road surface friction measuring rubber attached strip 50 to the main body 15, the shaft of the attaching bolt 31 is inserted through (the end opening of) the insertion part 50AA of the attaching bolt insertion slit 50A in the road surface friction measuring rubber attached strip 50 as illustrated in FIG. 10A and FIG. 10B. At this time, the attaching bolt 31 is in a state of being loosened to such an extent that it does not detach from the holder 35 (being fixed to the main body 15).

In the state in FIG. 10A and FIG. 10B, the vicinity of the end on the attachment part side (the side opposite to the friction measuring rubber 50B) of the road surface friction measuring rubber attached strip 50 is not in close contact with the rubber attached strip attachment part 35A of the holder 35.

Then, the road surface friction measuring rubber attached strip 50 is moved in an arrow D direction (rightward in FIG. 10A) in FIG. 10A relative to the attaching bolt 31 and the shaft of the attaching bolt 31 is relatively moved leftward along the insertion part 50AA of the attaching bolt insertion slit 50A so as to position the shaft of the attaching bolt 31 on the widthways center of the road surface friction measuring rubber attached strip 50. On this occasion, (the shaft of) the attaching bolt 31 abuts on the center-side end (that is, the end of the center part 50AB) of the attaching bolt insertion slit 50A and is positioned.

Figure 11A:
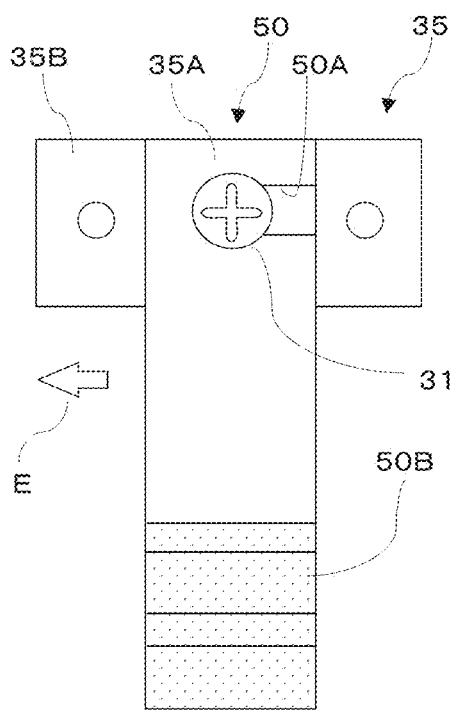
FIG. 11A is an explanatory diagram illustrating one example of a state where the road surface friction measuring rubber attached strip is moved from the state illustrated in FIG. 10A and FIG. 10B and the attaching bolt has been screwed into the main body of the friction coefficient measurement apparatus.
Figure 11B:
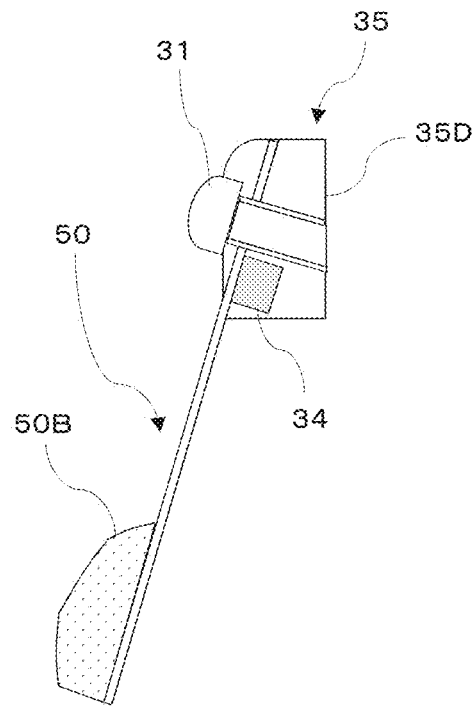
FIG. 11B is an explanatory diagram illustrating one example of the state where the road surface friction measuring rubber attached strip is moved from the state illustrated in FIG. 10A and FIG. 10B and the attaching bolt has been screwed into the main body of the friction coefficient measurement apparatus.

In this state, (the shaft of) the attaching bolt 31 is positioned on the center part 50AB of the attaching bolt insertion slit 50A and the vicinity of the end on the attachment part side (the side opposite to the friction measuring rubber 50B) of the road surface friction measuring rubber attached strip 50 is in close contact with the rubber attached strip attachment part 35A of the holder 35 (a state in FIG. 11A and FIG. 11B).

The road surface friction measuring rubber attached strip 50 is attached to the main body 15 of the friction coefficient measurement apparatus 101 via the holder 35 by fastening the attaching bolt 31 in the state in FIG. 11A and FIG. 11B.

Incidentally, since, also in the second embodiment, the rubber attached strip holding magnet 34 is embedded in the rubber attached strip attachment part 35A of the holder 35 and the road surface friction measuring rubber attached strip 50 whose part other than the friction measuring rubber 50B is constructed by the magnetic body is attracted to the rubber attached strip holding magnet 34 as illustrated in FIG. 10A, FIG. 10B, FIG. 11A and FIG. 11B similarly to the first embodiment, separation of the road surface friction measuring rubber attached strip 50 from the main body 15 side is prevented.

When detaching the road surface friction measuring rubber attached strip 50 that the friction measuring rubber 50B thereof has been worn down from the main body 15, the attaching bolt 31 is loosened (unscrewed) in a range that the attaching bolt 31 is not detached from the holder 35 in FIG. 11A and FIG. 11B. Then, the road surface friction measuring rubber attached strip 50 is moved in an arrow E direction (leftward in FIG. 11A) in FIG. 11A and the shaft of the attaching bolt 31 is detached from the attaching bolt insertion slit 50A in the road surface friction measuring rubber attached strip 50. On this occasion, detachment is performed while avoiding interference with the part 35B which is larger in thickness than the rubber attached strip attachment part 35A by pulling upward the left-side end of the road surface friction measuring rubber attached strip 50 in the direction vertical to the drawing and in the spectator-side direction.

It is possible to detach the road surface friction measuring rubber attached strip 50 that the friction measuring rubber 50B thereof has been worn down from the main body 15 of the friction coefficient measurement apparatus 101 in this way.

Other constructions and operational effects of the second embodiment illustrated in FIG. 9A, FIG. 9B, FIG. 10A, FIG. 10B, FIG. 11A and FIG. 11B are the same as those of the first embodiment illustrated in FIG. 1, FIG. 2, FIG. 3A, FIG. 3B, FIG. 4A, FIG. 4B, FIG. 5A, FIG. 5B, FIG. 6A, FIG. 6B, FIG. 7 and FIG. 8.

Next, points of the friction coefficient measurement apparatuses 100 (101) according to the illustrated first and second embodiments which are different from those of the related art friction coefficient measurement apparatus (the Patent literature 1 and so forth) will be mainly described with reference to FIG. 12.

Figure 12:
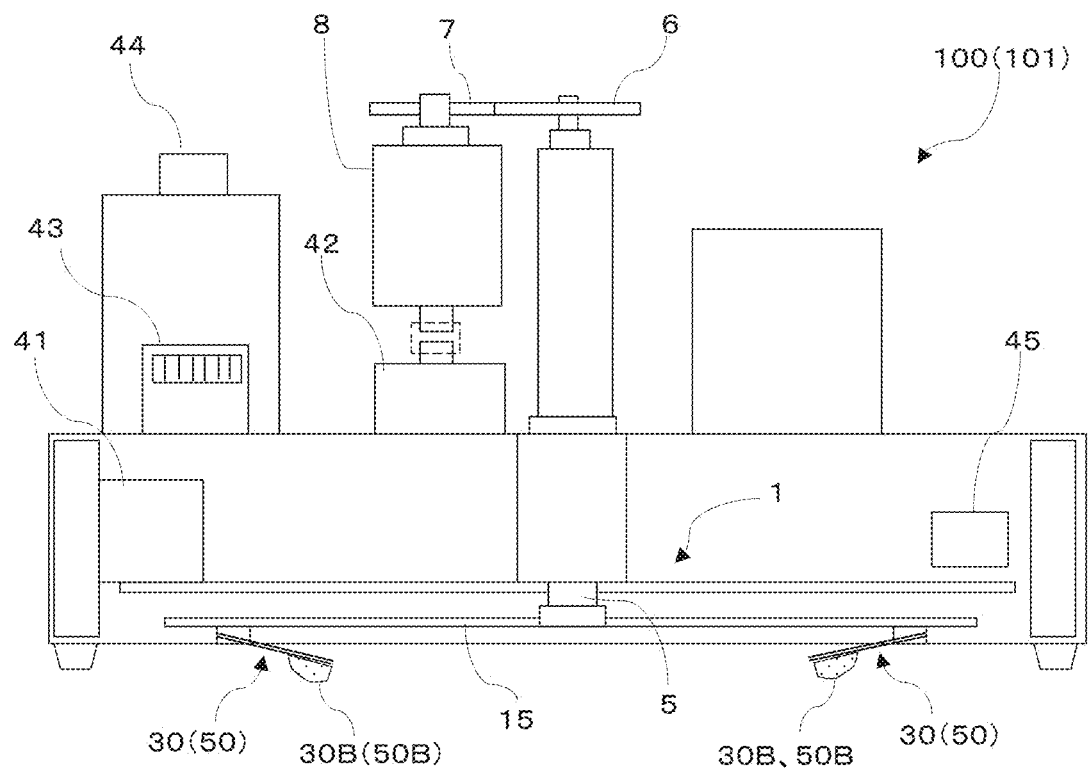
FIG. 12 is an explanatory diagram illustrating one example of the friction coefficient measurement apparatus according to the first or second embodiment.

In FIG. 12, the friction coefficient measurement apparatus 100 (101) includes the inclinometer 41. An article on the market (for example, a brand name "DS Series" manufactured by NKK SWITCHES CO. LTD.) may be used as the inclinometer 41.

The inclinometer 41 has the function of measuring the inclination of the whole friction coefficient measurement apparatus 100 (101). A measurement result obtained from the inclinometer 41 is sent to the electromagnetic brake 42 via a not illustrated signal transfer line.

In FIG. 12, the driving motor 8 rotates the friction measurement unit 1 via the gears 6 and 7 and the shaft 5. Then, the road surface friction measuring rubber attached strips 30 (50) are attached onto the lower surface of the main body 15 of the friction measurement unit 1, for example, at three positions.

Although not clearly illustrated in FIG. 12, the electromagnetic brake 42 has the function that in a case where the inclination of the friction coefficient measurement apparatus 100 (101) which is at least a predetermined angle has been measured by the inclinometer 41 in a state where the friction coefficient measurement apparatus 100 (101) is in operation, (the electromagnetic brake 42) operates and stops the operation of the friction coefficient measurement apparatus 100 (101).

In addition, the electromagnetic brake 42 also has the function that in a case where the friction coefficient measurement apparatus 100 (101) which is in operation has been lifted manually, the electromagnetic brake 42 operates and stops the operation of the friction coefficient measurement apparatus 100 (101).

In addition, the friction coefficient measurement apparatus 100 (101) according to the illustrated embodiment includes the counter 43. The counter 43 has the function of measuring and displaying the number of operations or the number of measurements of the friction coefficient measurement apparatus 100 (101).

The number of operations or the number of measurements which is displayed on the counter 43 serves as the index for indicating to what extent the friction measuring rubber 30B (50B) of the road surface friction measuring rubber attached strip 30 (50) in the friction coefficient measurement apparatus 100 (101) is worn down and it is possible for a user of the friction coefficient measurement apparatus 100 (101) to grasp the timing of replacing the road friction measuring rubber attached strip 30 (50) with the new one.

Further, in the illustrated embodiment, the friction coefficient measurement apparatus 100 (101) includes the satellite positioning system 44 (for example, the global positioning system: GPS). Although illustration is omitted, position information of the friction coefficient measurement apparatus 100 (101) determined by the satellite positioning system 44 is sent to a processing device in the friction coefficient measurement apparatus 100 (101) or an externally disposed processing system and thereby it becomes possible to accurately determine the position where the friction coefficient has been measured by the friction coefficient measurement 100 (101).

The friction coefficient measurement apparatus 100 (101) according to the illustrated embodiment also includes the road surface temperature measurement device 45. The road surface temperature measurement device 45 has the function of measuring the road surface temperature when measuring the friction coefficient of the road surface. Therefore, it is possible to determine the accurate friction coefficient by analyzing the influence of the road surface temperature imposed on the friction coefficient of the road surface and taking the road surface temperature into consideration.

It is to be additionally noted that the illustrated embodiments are merely illustrative and are not described with the intention of limiting the technical scope of the present invention. For example, friction coefficient measurement apparatuses of the types other than those illustrated in FIG. 1 and FIG. 2 are also applicable.

DESCRIPTION OF REFERENCE NUMERALS OR SYMBOLS 30, 50 . . . road surface friction measuring rubber attached strip
30A . . . attaching bolt insertion opening
30AA . . . large-diameter circular part (of the opening)
30AB . . . small-diameter circular part (of the opening)
31 . . . attaching bolt
32 . . . anti-loosening spring washer (existing spring washer)
33 . . . rubber attached strip fall prevention washer
33A . . . notch
33B . . . projection
34 . . . rubber attached strip holding magnet
41 . . . inclinometer
42 . . . electromagnetic brake
43 . . . counter
44 . . . satellite positioning system
45 . . . road surface temperature measurement device
50A . . . attaching bolt insertion slit
100, 101 . . . friction coefficient measurement apparatus

The invention claimed is:
1. A friction coefficient measurement apparatus, which measures an angle of relative torsion caused by a friction between a road surface friction measuring rubber attached strip and a road surface and the friction coefficient measurement apparatus which is able to reduce operation taken for work of replacing the road surface friction measuring rubber attached strip with a new one, the friction coefficient measurement apparatus comprising:
 a road surface friction measuring rubber attached strip and an attaching bolt which attaches the road surface friction measuring rubber attached strip to the friction coefficient measurement apparatus;

an attaching bolt insertion opening formed in the road surface friction measuring rubber attached strip, the attaching bolt insertion opening having a shape formed by overlapping circles of different diameter sizes, a diameter of a large-diameter circular part being set larger than a diameter of a bolt head of the attaching bolt and a diameter of a small-diameter circular part being set smaller than the diameter of the bolt head of the attaching bolt and larger than a diameter of a bolt shaft; and a rubber attached strip fall prevention washer interposed between an attaching bolt anti-loosening spring washer and the bolt head of the attaching bolt, the rubber attached strip fall prevention washer being formed into an annular shape, a notch being formed therein and a plurality of projections which project outwardly in a radius direction being formed thereon, an opening size of said notch being set smaller than an outer diameter of the shaft of the attaching bolt and a maximum distance between leading ends of the projections being set larger than a large diameter of the attaching bolt insertion opening formed in the road surface friction measuring rubber attached strip.

2. The friction coefficient measurement apparatus according to claim 1, wherein
the road surface friction measuring rubber attached strip is constructed by a magnetic body and a rubber attached strip holding magnet is provided in the vicinity of the attaching bolt.

3. The friction coefficient measurement apparatus according to claim 1, further comprising an inclinometer which measures an inclination.

4. The friction coefficient measurement apparatus according to claim 1, further comprising a counter.

5. The coefficient measurement apparatus according to claim 1, further comprising a satellite positioning system.

6. The friction coefficient measurement apparatus according to claim 1, further comprising a road surface temperature measurement device which measures a road surface temperature.

7. A friction coefficient measurement apparatus, which measures an angle of relative torsion caused by a friction between a road surface friction measuring rubber attached strip and a road surface and the friction coefficient measurement apparatus which is able to reduce operation taken for work of replacing the road surface friction measuring rubber attached strip with a new one, the friction coefficient measurement apparatus comprising:

a road surface friction measuring rubber attached strip and an attaching bolt which attaches the road surface friction measuring rubber attached strip to the friction coefficient measurement apparatus;

an attaching bolt insertion slit formed from one side surface toward pass the center of the road surface friction measuring rubber attached strip, the attaching bolt insertion slit being formed from one side surface toward the center side of the road surface friction measuring rubber attached strip, the attaching bolt insertion slit being set to a width size which is smaller than a diameter of a bolt head of the attaching bolt and being larger than a diameter of a bolt shaft thereof and set into a semicircular shape a diameter size of which is smaller than the diameter of the bolt head of the attaching bolt and is larger than the diameter of the bolt shaft of the attaching bolt on the widthways center of the road surface friction measuring rubber attached strip;

a rubber attached strip fall prevention washer interposed between an attaching bolt anti-loosening spring washer and the bolt head of the attaching bolt, the rubber attached strip fall prevention washer is formed into an annular shape, a notch being formed therein and a plurality of projections which project outwardly in a radius direction being formed thereon, an opening size of said notch being set smaller than an outer diameter of the shaft of the attaching bolt and a maximum distance between leading ends of the projections being set larger than the width of the attaching bolt insertion slit.

8. The friction coefficient measurement apparatus according to claim 7, wherein
the road surface friction measuring rubber attached strip is constructed by a magnetic body and a rubber attached strip holding magnet is provided in the vicinity of the attaching bolt.

9. The friction coefficient measurement apparatus according to claim 7, further comprising an inclinometer which measures an inclination.

10. The friction coefficient measurement apparatus according to claim 7, further comprising a counter.

11. The friction coefficient measurement apparatus according to claim 7, further comprising a satellite positioning system.

12. The friction coefficient measurement apparatus according to claim 7, further comprising a road surface temperature measurement device which measures a road surface temperature.

\* \* \* \* \*